United States Patent [19]
Young et al.

[11] Patent Number: 5,873,980
[45] Date of Patent: Feb. 23, 1999

[54] APPARATUS AND METHOD FOR RECOVERING SOLVENT

[75] Inventors: Gerald P. Young; Gerald L. Portis, both of Seabrook; John M. Yardley, Baytown, all of Tex.

[73] Assignee: Houston Industries Incorporated, Houston, Tex.

[21] Appl. No.: 865,497

[22] Filed: May 29, 1997

[51] Int. Cl.[6] .............................. B01D 3/42; B01L 11/00
[52] U.S. Cl. .............................. 203/1; 422/100; 422/101; 422/256; 73/61.59; 203/87; 203/DIG. 2; 202/176; 202/186; 202/185.6; 196/98
[58] Field of Search ............................. 422/99, 100, 101, 422/256, 260; 73/61.43, 61.59; 203/10, 39, DIG. 2, 87, 1; 202/185.6, 176, 205, 186; 196/98; 159/26.2

[56] References Cited

U.S. PATENT DOCUMENTS

| | | | |
|---|---|---|---|
| 3,626,751 | 12/1971 | Overbeck et al. | 73/61.1 |
| 3,776,695 | 12/1973 | Peterson | 23/230 PC |
| 3,908,443 | 9/1975 | Hokansson | 73/61.1 |
| 3,972,693 | 8/1976 | Wiesner et al. | 55/42 |
| 4,004,453 | 1/1977 | Thyrum | 73/61.1 R |
| 4,238,451 | 12/1980 | Ciais et al. | 422/101 |
| 4,308,244 | 12/1981 | Sikdar et al. | 423/339 |
| 4,430,888 | 2/1984 | Lepain et al. | 73/61.1 |
| 4,624,133 | 11/1986 | Iwashita | 73/61.1 R |
| 4,656,141 | 4/1987 | Birks et al. | 436/172 |
| 4,741,835 | 5/1988 | Jacques et al. | 210/708 |
| 4,839,043 | 6/1989 | Broussard, Sr. | 210/195.1 |
| 5,009,787 | 4/1991 | Broussard, Sr. | 210/634 |
| 5,011,571 | 4/1991 | Kobayashi et al. | 159/47.3 |
| 5,033,288 | 7/1991 | Castel | 73/61.11 R |
| 5,089,152 | 2/1992 | Flynn et al. | 252/194 |
| 5,100,546 | 3/1992 | Broussard, Sr. | 210/195 |
| 5,294,553 | 3/1994 | Kawahara | 436/60 |

OTHER PUBLICATIONS

Standard Methods for the Examination of Wastewater, Sixteenth Edition, prepared and published by American Public Health Association, American Water Works Association and Water Pollution Control Federation, pp. 496–501. No Date Available.

Standard Methods for the Examination of Wastewater, Eighteenth Edition, Oil and Grease 5520B, pp. 5–24 to 5–27. No Date Available.

Oil and Grease, Total, Recoverable, Method 413.1, (Gravimetric, Separatory Funnel Extraction), EPA Procedures Manual in EDC Central Lab, Issued 1974, Editorial revision 1978, pp. 413.1–1 to 413.1–3.

Method 1664, N–Hexane Extractable Material (HEM) and Silica Gel Treated N–Hexane Extractable Material (SGT–HEM) by Extraction and Gravimetry (Oil and Grease and Total Petroleum Hydrocarbons), U.S. EPA Office of Water, 21 pages. No Date Available.

General catalog of Scientific Glass & Instruments, Inc. of Houston, Texas LE–74, 1974, front cover and pp. 4, 9, 53, 58,60, 61, 65, 78, Distillation Apparatus cover sheet, 92, 98, 102, Evaporative and Extraction Apparatus cover sheet, 111, 112, 114, 115, and back cover page. No Date Available.

The Complete Laboratory Glassware Catalog 1994–95, Baxter Scientific Products, Baxter Healthcare Corporation 1994, title page, and pp. 4, 14, 407, 411, 413,414, 430, 504, 505, 525, 528, 530, 541, 545, 560, 580, 600, 627, 667 and 756.

*Primary Examiner*—Robert Warden
*Assistant Examiner*—Fariborz Moazzam
*Attorney, Agent, or Firm*—Pravel, Hewitt & Kimball

[57] ABSTRACT

A solvent recovery system for an oil and grease test collects and condenses solvent vapors to recover solvent. A vessel having an inlet for sealingly receiving an outlet of a separatory funnel receives solvent from the separatory funnel. The solvent is filtered through a filter paper placed in a funnel integral with the vessel. The funnel has a lower tubular section protruding from the vessel. A vapor return tube, integral with the vessel, surrounds the tubular section providing an annular space between an inside wall of the vapor return tube and an outside wall of the tubular section. Filtrate flows downward through the funnel tubular section into an evaporation flask, where the solvent is heated and evaporated leaving an oil and grease residue. Solvent vapors flow upward through the annular space within the vapor return tube into the vessel. A condenser, integral with the vessel, receives and condenses the vapors forming a condensate that is collected in a solvent recovery flask.

19 Claims, 4 Drawing Sheets

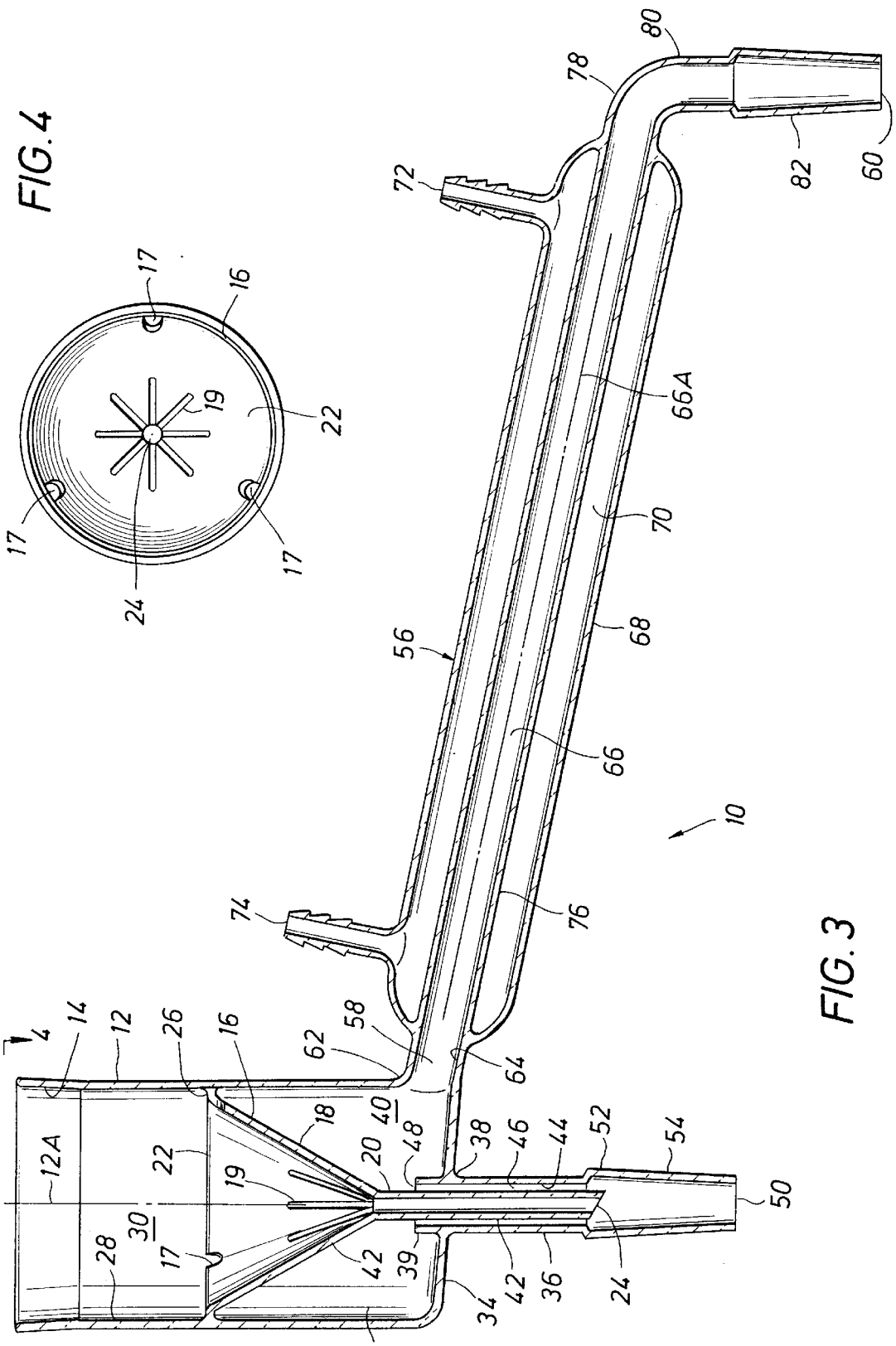

APPARATUS AND METHOD FOR RECOVERING SOLVENT

BACKGROUND OF THE INVENTION

1. Field of the Invention

The present invention relates to an oil and grease analysis for wastewater, and more particularly, to recovery of solvent used in the oil and grease analysis.

2. Description of the Related Art

Wastewater discharged from industrial and municipal wastewater treatment plants is typically tested for oil and grease content. A standard method used in performing this test involves the intimate mixing of a sample of wastewater with a solvent for extracting oil and grease from the wastewater sample. The solvent presently used is heavier than water and readily separate from the water, settling to the bottom of the mixing vessel. As illustrated in FIG. 1, the mixing vessel used is typically a separatory funnel SF. The solvent and extracted oil and grease is filtered through a filter paper FP in a filter funnel FF and collected in a clean, dry collection flask CF of known weight. The solvent is evaporated in a hood H with solvent passing into the atmosphere via an exhaust opening EO, and the dry flask CF is then weighed again. The difference in the weight of flask CF is the oil and grease content, which remains in flask CF as a residue after the solvent is evaporated. The difference in the two weights, expressed as a ratio to the original sample weight, is the percentage of oil and grease in the wastewater.

Presently, the oil and grease tests are conducted according to United States Environmental Protection Agency (EPA) Methods 413.1 or 5520B. The solvent used for Methods 413.1 or 5520B is a trichlorotrifluoroethane specifically, 1,1,2-trichloro-1,2,2-trifluoroethane, available from E. I. DuPont de Nemours & Company under the registered trademark FREON (referred to hereinafter as "chlorofluorocarbon"). Chlorofluorocarbon has been widely used as an effective solvent useful in the determination of oil and grease because of its solvent power for oils, greases, waxes and the like. However, chlorofluorocarbons in the atmosphere have been identified as a primary contributor to the degradation of an ozone layer in the earth's upper atmosphere. Chlorofluorocarbon is also quite expensive. So ongoing wastewater analysis for oil and grease content is somewhat expensive because the chlorofluorocarbon is evaporated to the atmosphere.

U.S. Pat. No. 5,294,553, assigned on its face to the EPA, is incorporated by reference herein for all purposes. The '553 patent discloses a review of technology available for the gravimetric determination of oil and grease. The EPA has recently published a Method 1664 which replaces chlorofluorocarbon in oil and grease analysis, with hexane as the solvent. Paragraphs 6.6 and 11.4 of Method 1664 call for recovering solvent during solvent evaporation using a distilling head claisen, a distilling adapter and a solvent collection flask. However, in this Method 1664, before the step of evaporation, hexane is drained openly from a separatory funnel through a filter funnel into a boiling flask. During this filtration step, solvent evaporates into the atmosphere, which both potentially exposes the analyst to the vapors and contributes to solvent losses. Consequently, a need remains for an apparatus and method for conducting oil and grease analyses, while minimizing solvent losses to the atmosphere.

SUMMARY OF THE INVENTION

A solvent recovery system for an oil and grease test collects and condenses solvent vapors to recover solvent. A vessel having an inlet for sealingly receiving an outlet of a separatory funnel receives solvent from the separatory funnel. The solvent is filtered through a filter paper placed in a funnel integral with the vessel. The funnel has a lower tubular section protruding from the vessel. A vapor return tube, integral with the vessel, surrounds the tubular section providing an annular space between an inside wall of the vapor return tube and an outside wall of the tubular section. Filtrate flows downward through the funnel tubular section into an evaporation flask, where the solvent is heated and evaporated leaving an oil and grease residue. Solvent vapors flow upward through the annular space within the vapor return tube into the vessel. A condenser, integral with the vessel, receives and condenses the vapors forming a condensate that is collected in a solvent recovery flask.

BRIEF DESCRIPTION OF THE DRAWINGS

The objects, advantages and features of the invention will become more apparent by reference to the drawings which are appended hereto, wherein like numerals indicate like parts and wherein an illustrated embodiment of the invention is shown, of which:

FIG. 3 is cross section of a solvent recovery apparatus according to the present invention.

FIG. 4 is a top view of a cylindrical vessel portion of FIG. 3 as seen along the lines 4—4.

DETAILED DESCRIPTION OF THE PREFERRED EMBODIMENTS

Since evaporating chlorofluorocarbons into the atmosphere is undesirable due to environmental and cost concerns, an investigation was undertaken to identify a solution. No commercially-available apparatus was found that filtered solvent from a separatory funnel into a boiling or evaporation flask and allowed for evaporation, condensation and solvent recovery in a closed system.

However, laboratory glassware for solvent filtration and evaporation is commercially available from several manufacturers including Kimble Science Products and Kontes Chemistry and Life Sciences Products. For example, Baxter Healthcare Corporation, Scientific Products (referred to hereinafter as "Baxter Scientific Products") sells Kimble and Kontes glassware and laboratory equipment and provides filtration equipment, separatory funnels, filter funnels, evaporators, distillation heads and associated glassware, flasks, condensers and many other items. A prototype solvent recovery system was built using standard laboratory glassware to determine that solvent could be recovered and that solvent losses could be reduced in an oil and grease analysis.

Figure 2:
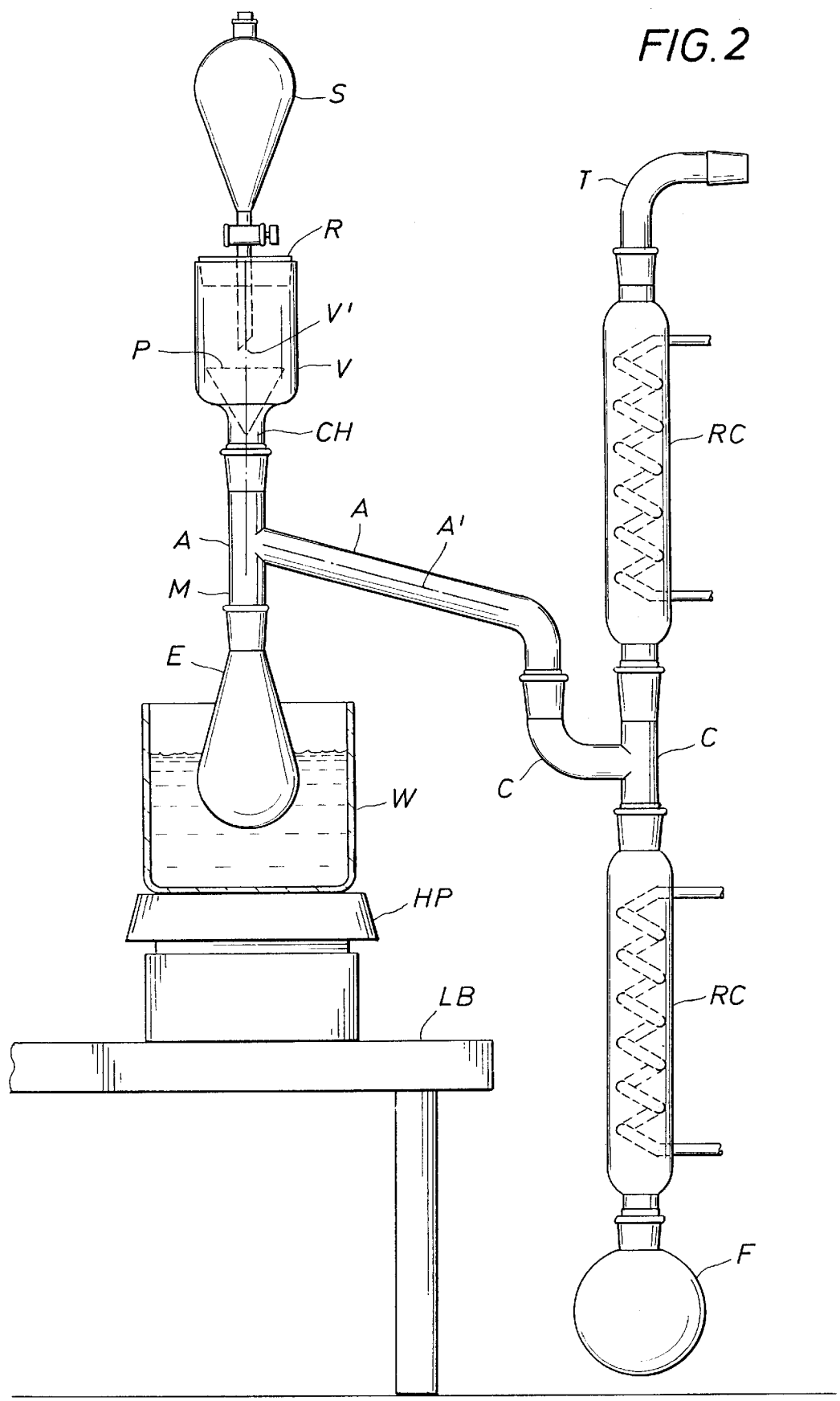
FIG. 2 is an elevational view of a solvent recovery system according to the present invention as assembled from standard laboratory glassware.

Part numbers are with reference to Baxter Scientific Products' 1994–95 laboratory glassware catalog, and with reference to FIG. 2, a No. 636031-2000 standard laboratory glassware separatory funnel S (2,000 ml) was fitted to a No.

150100-0451 reducing adapter or vessel V having a longitudinal axis V' with a rubber stopper R. A No. F2605-12S Whatman phase separator filter paper P was placed inside vessel V to filter particulate from a wastewater sample. A chamber CH is thereby defined in the vessel V. A No. 211410-2440 transfer adapter A was connected to a No. 601000-0424 250 ml round bottom evaporation or boiling flask E directly below vessel V for receiving filtered liquid solvent extract from separatory funnel S, the extract containing oil and grease extracted from the wastewater sample. The vertical portion of adapter A provides a vapor return member M to the downwardly sloped portion of adapter A having a longitudinal axis A'.

Transfer adapter A was connected at its other outlet to a Claisen distillation adapter C, which was connected in between two reflux condensers RC (No. 457000-0225 or 456900-3024). A 100 ml solvent recovery flask F was connected to the bottom of the lower reflux condenser RC for recovering solvent condensed in reflux condensers RC. The top of the upper reflux condenser RC was connected to one end of a tube adapter T, and the other end of tube adapter T was connected to one end of a tube (not shown), the other end of the tube being sealed by insertion in water at ground level.

Solvent and water were mixed intimately in the separatory funnel S to extract oil and grease into the solvent. Filter paper P was placed within vessel V, and separatory funnel S was sealed to vessel V using rubber stopper R. Solvent was drained from separatory funnel S through the filter paper P into evaporation flask E. Resting on a laboratory bench LB, a hot plate HP heated a water bath W, which heated evaporation flask E to evaporate the solvent, leaving the oil and grease in evaporation flask E as a residue. Solvent vapors rose and passed through transfer adapter A into reflux condensers RC, where the solvent vapors were condensed into liquid solvent. Liquid solvent drained into recovery flask F, where it was available for reuse.

A closed solvent recovery system was thus built from standard components, and about 80 to 95 percent, typically about 93 percent, of the solvent was recovered. However, the apparatus was large and unwieldy, measuring about three feet high between laboratory bench LB and the top of separatory funnel S and about four to five feet high between solvent recovery flask F and the top of tube adapter T. The apparatus takes up a great deal of space and is far too large to be placed in a fume hood. However, the apparatus was useful for proving that an oil and grease measurement could be made using a closed system that reduced solvent losses, and the apparatus and system described below was subsequently developed.

With reference to FIGS. 3 and 4, a preferred embodiment of a solvent recovery apparatus, generally indicated at 10, is illustrated according to the present invention. Solvent recovery apparatus 10 is preferably sized for use on a laboratory bench and is preferably fabricated from standard laboratory glassware such as borosilicate, which is available under the trademark "PYREX". Glass is preferred since it allows an analyst to see inside the apparatus, but the size and material of construction can be altered to suit the needs of a particular application. A cylindrical vessel 12 having a longitudinal axis 12A has an outwardly extending frustroconical rim 14 tooled for receiving a standard number 13½ rubber stopper. Vessel 12 can be fabricated from, for example, standard wall glass tubing having an outside diameter of 70 mm and a length of 110 mm. A fluted filter funnel 16 has three equidistant spaced notches 17, an upper conical portion 18, grooves 19, and a lower tubular portion 20. Filter funnel 16 has an enlarged area inlet 22 and a reduced area outlet 24. A juncture rim 26, which defines inlet 22, is welded to an inside wall 28 of vessel 12, dividing vessel 12 into an upper portion 30 and a lower portion 32.

Vessel 12 has, preferably, a sloped bottom 34, and a vapor return tube 36 is preferably formed integral with bottom 34 or, alternatively, sealed in an opening in bottom 34. A seal 38 is formed between bottom 34 and vapor return tube 36 in either case. Vapor return tube 36 is about 90 mm in length and projects into vessel 12 forming a continuous cylindrical lip 39 inside vessel 12. A chamber 40 is defined within vessel 12 when a stopper is engaged with rim 14, as discussed below in detail. Filter funnel 16 has an outside wall 42. Vapor return tube 36 has an inside wall 44. Inside wall 44 and outside wall 42 of tubular portion 20 of filter funnel 16 define an annular space 46, which is in fluid communication with chamber 40 through an annular opening 48. An opening 50 is provided at a lower end of vapor return tube 36, and outlet 24 of filter funnel 16 is preferably located below annular opening 48 and above opening 50, but tubular portion 20 of filter funnel 16 can be extended so that outlet 24 is located below opening 50. Vapor return tube 36 has a lower portion 52, which terminates in a standard taper 24/40 ground glass joint 54 for sealing solvent recovery apparatus 10 with a conventional evaporation flask.

A condenser, generally indicated at 56, is preferably formed integral with or is otherwise sealed to vessel 12 at bottom 34 so that liquid will drain by gravity through an inlet 58 into condenser 56. Condenser 56 has an outlet 60, and a seal 62 is formed with vessel 12 at inlet 58. A tube 64 defines a passageway 66 between inlet 58 and outlet 60. Passageway 66 has a longitudinal axis 66A which is sloped at an angle α, angle α being preferably about ten degrees (10°) from horizontal line H when longitudinal axis 12A is in a vertical position so that liquid will drain from bottom 34 to outlet 60. A water jacket 68 around tube 64 forming an annular space 70 within water jacket 68 and outside of an outside surface 76 of tube 64. A tube inlet connector 72 and a tube outlet connector 74 are formed integral with water jacket 68 for receiving and discharging, respectively, a coolant flowing through annular space 70. Tube 64 has a bend 78 providing a one hundred degree (100°) transition into a vertical outlet portion 80, which terminates in a standard ground glass joint 82 for sealing solvent recovery apparatus 10, as described below. Condenser 56 is a nonstandard Liebig condenser, the outside diameter of tube 64 being about 15 mm and the lateral distance between opening 50 of vapor return tube 36 and outlet 60 of condenser 56 being about 300 mm.

Figure 5:
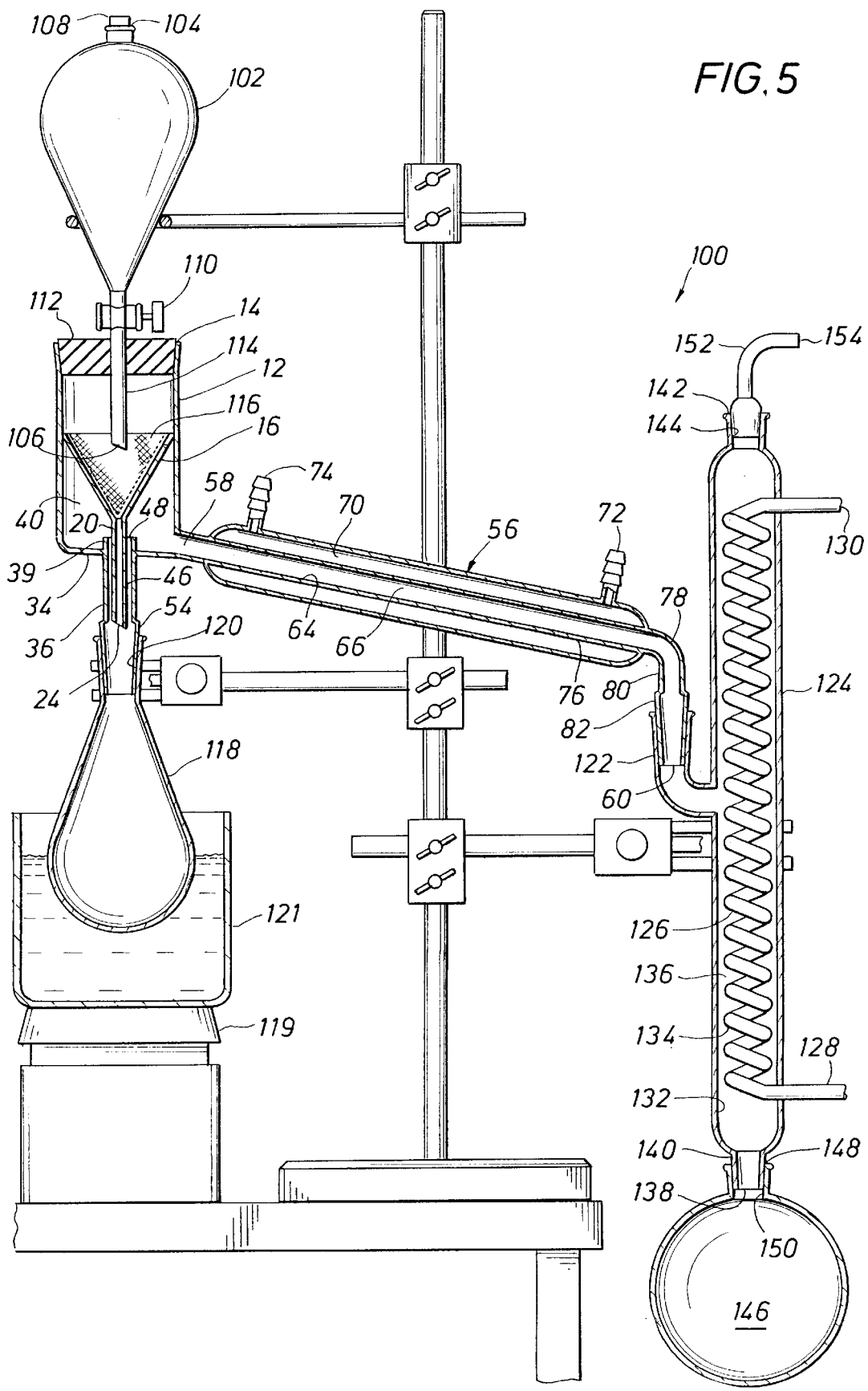
FIG. 5 is an elevational view and a partial cross section of a solvent recovery system according to the present invention.

As illustrated in FIG. 5, solvent recovery apparatus 10 is used in conjunction with other components to form a solvent recovery system 100. A conventional separatory funnel 102 has an inlet 104 and an outlet 106. A stopper 108 seals inlet 104, and a stop cock 110 is provided for draining the contents of separatory funnel 102 through outlet 106. A stopper 112, sized to form a vapor-tight seal with rim 14 of vessel 12, is placed over a tubular portion 114 of separatory funnel 102. Before stopper 112 is sealed with rim 14, a filter paper 116 is placed in filter funnel 16. An evaporation flask 118, having an inlet 120, is removably sealed with ground glass joint 54 of vapor return tube 36. A hot plate 119 heats a water bath 121 for applying heat to evaporation flask 118.

Ground glass joint 82 of condenser 56 seals with a side port 122 of an elongated single chamber reflux condenser 124. Reflux condenser 124 has a cooling coil 126, which has an inlet 128 and an outlet 130. Reflux condenser 124 has an inside wall 132. Cooling coil 126 has an outside wall 134.

A space or chamber 136 is defined between wall 132 and wall 134. Reflux condenser 124 has a lower outlet 138 defined by a ground glass joint 140 and an upper outlet 142 defined by a ground glass joint 144. A solvent recovery flask 146, having an inlet 148 defined by a ground glass joint 150, is sealed with ground glass joint 140. A ground glass joint of a tubing adapter 152 seals with ground glass joint 144, providing a vent 154 for solvent recovery system 100, as discussed below.

Figure 6:
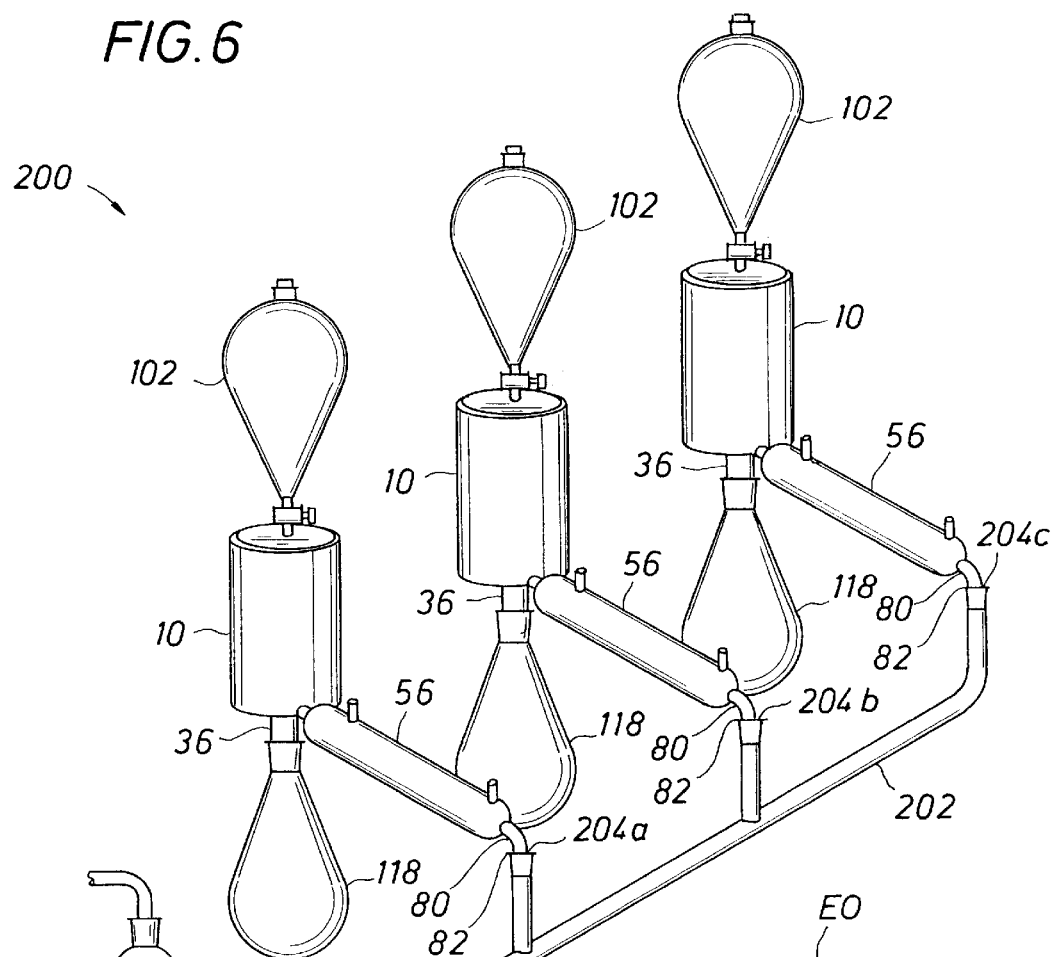
FIG. 6 is a perspective view of a solvent recovery system for handling multiple samples simultaneously according to the present invention.
Figure 1:
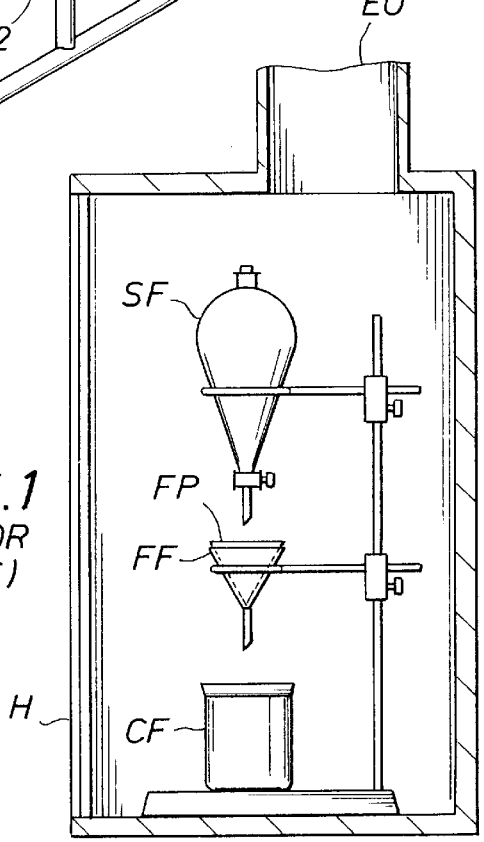
FIG. 1 is an elevational view and partial cross section of a prior art filtration set up.

Turning now to FIG. 6, a solvent recovery system 200, which manifolds several solvent recovery apparatus 10, is illustrated according to the present invention. A manifold 202 has inlets 204a, 204b and 204c defined by ground glass joints for sealing with ground glass joint 82 of condenser 56 of the present invention. Manifold 202 drains through an outlet 206 into a side port 122' of a reflux condenser 124', which is likely larger than reflux condenser 124 since several solvent apparatus 10 are manifolded together. A solvent recovery flask 146' is sealed with reflux condenser 124'.

Method of Operation

The apparatus is thus described, and its method of use is believed to comply with EPA Methods 413.1 and 5520B for chlorofluorocarbon solvent and with Method 1664 when hexane is used as the solvent. Filter paper 116, such as Whatman phase separator paper, is placed in filter funnel 16 and, if necessary for additional water removal, a chemical drying agent, such as anhydrous sodium bisulfate, which is required in Method 1664, can be placed in filter paper 116. Evaporation flask 118 is cleaned, dried, weighed and sealed to ground glass joint 54. The apparatus is preferably assembled as illustrated in FIGS. 5 or 6, except that separatory funnel 102 is not yet sealed to vessel 12. Solvent is mixed intimately with a measured quantity of wastewater in separatory funnel 102 to extract oil and grease from the wastewater into the solvent. If the solvent is lighter than water, as hexane is, then the water settles to the bottom of the separatory funnel and is drained off before sealing separatory funnel 102 to vessel 12. If the solvent is heavier than water, as chlorofluorocarbon is, then the solvent settles to the bottom of separatory funnel 102, and separatory funnel 102 is sealed with rubber stopper 112 to vessel 12 with the water remaining inside separatory funnel 102.

Stopcock 110 is opened to drain the solvent out of separatory funnel 102 and into filter funnel 16. The solvent is filtered to remove particulate matter and water, the solvent flowing through filter paper 116 into grooves 19 and discharging through outlet 24. The solvent is collected in evaporation flask 118, and sufficient heat is applied to evaporation flask 118 using hot plate 119 and water bath 121 to evaporate the solvent. As solvent is evaporated, vapors rise and pass through annular space 46 into chamber 40. The length of tubular portion 20 of filter funnel 16 and the cross-sectional area of annular space 46 are sized so that droplets falling from tubular portion 20 are not carried upward by vapor rising through annular space 46. Tubular portion 20 and annular space 46 are advantageous in that liquid solvent can only drain into evaporation flask 118 and cannot bypass evaporation flask 118 by flowing directly into condenser 56, while annular space 46 provides a flow path for solvent vapors to flow into chamber 40 and then into condenser 56. Warm vapor in chamber 40 vaporizes any solvent remaining in filter paper 116, which reduces solvent losses when filter paper 116 is discarded.

Cooling water flows into annular space 70 of condenser 56 through inlet 72 and cools inner tube 64. Since condenser 56 is cool relative to vessel 12 and is in physical contact with vessel 12, a thermodynamic effect is created which draws solvent vapors from vessel 12 into condenser 56. Pressure is lower in passageway 66, due to cooling, than in chamber 40. One advantage of this thermodynamic effect is that it helps to dry filter paper 116 in filter funnel 16 which reduces solvent losses. As some vapor condenses in chamber 40, lip 39 prevents liquid condensate from draining into annular space 46. Solvent vapor flows from chamber 40 into passageway 66, and a portion of the vapor is condensed. Solvent vapor and condensate then flows through passageway 66 of condenser 56 into side port 122 of reflux condenser 124. Reflux condenser 124 completes the condensation of the vapors, and condensate is collected in solvent recovery flask 146, where it is available for reuse. With solvent recovery system 200, multiple samples of wastewater can be analyzed simultaneously.

Solvent recovery system 100 is closed and sealed except for vent 154, which may connected by tubing to a water seal. It is believed that solvent recovery system 100 can recover over 95 percent, and possibly over 99 percent, of the solvent introduced into separatory funnel 102. After all of the solvent is evaporated from evaporation flask 118, a residue of oil and grease from the wastewater sample is left in evaporation flask 118.

Evaporation flask 118 is removed from ground glass joint 54 and reweighed to determine the quantity of oil and grease by difference in weight.

When the solvent used is heavier than water, such as chlorofluorocarbon, it is preferable to use a midpoint side port such as side port 122 because cooling coil 126 below side port 122 provides sufficient subcooling for condensed solvent, while the upper portion of cooling coil 126 provides complete condensation of any vapors which rise. However, if the solvent used is lighter than water, such as a hexane-based solvent, then it is preferable to locate side port 122 closer to lower outlet 138 (not shown) so that more of cooling coil 126 is available to condense any vapors that tend to rise.

The present invention is advantageous for several reasons. Solvent losses are minimized, which reduces emissions of pollutants into the atmosphere and risk of personnel exposure to potentially harmful vapors. Operating expenses are also reduced since less solvent must be purchased to replace solvent lost into the atmosphere. Filtration is provided within a closed system since the separatory funnel is sealed to the vessel, and the filter funnel is sealed within the vessel. The tubular section of the funnel directs solvent into the evaporation flask so that the solvent does not flow directly into the condenser, which would create an error in the oil and grease measurement. The funnel is welded within the vessel so it does not get separated and lost. Solvent in the filter paper is evaporated and recovered. The vapor return tube and the condenser are welded to the vessel forming an integral seal. In the preferred embodiment, the only removable seals are the separatory funnel-vessel connection, vapor return tube-evaporation flask connection, condenser-side port connection, and reflux condenser-recovery flask connection, and thus, few joints can leak. Also, in the preferred embodiment, the lip on the vapor return tube prevents re-entry of solvent into the evaporation flask. The solvent recovery flask disassembles sufficiently for cleaning. Finally, the preferred embodiment of the solvent recovery apparatus is compact, requiring a minimal amount of valuable laboratory space.

The foregoing disclosure and description of the invention are illustrative and explanatory thereof, and various modifications and alterations to the embodiments disclosed herein will be apparent to those skilled in the art in view of this disclosure. It is intended that all such variations and modifications fall within the spirit and scope of this invention as claimed.

We claim:

1. An apparatus for recovering a solvent from a test sample/solvent mixture, comprising:
    a vessel having a chamber, an inlet for receiving the sample/solvent mixture, and an outlet;
    a filter holder funnel disposed within said vessel between said inlet and said outlet;
    said funnel having a lower tubular section extending from said filter holder funnel outwardly through said vessel outlet;
    a vapor return member with said vessel and being in fluid communication with said chamber to allow solvent flow from said chamber;
    said vapor return member surrounding a portion of said lower tubular section of said funnel to form an annular space at said vessel outlet between said tubular section and said vapor return member; and
    a condenser sealed with said vessel and being in fluid communication with said chamber for receiving and condensing vapors from said chamber.

2. The apparatus of claim 1, wherein said vessel has a rim around said inlet for receiving a stopper.

3. The apparatus of claim 1, wherein said vapor return member is integrally formed with said vessel.

4. The apparatus of claim 1, wherein
    said annular space between said tubular section and said vapor return member provides a fluid pathway for vapors to flow upward into said chamber.

5. The apparatus of claim 1, wherein said vapor return member includes an upper portion projecting into said chamber to form a lip inside said vessel chamber.

6. The apparatus of claim 1, wherein said vessel has a sloped bottom and a condenser port leading therefrom for draining solvent from said chamber into said condenser.

7. The apparatus of claim 1, wherein said vessel and said vapor return member are cylindrical and substantially coaxial.

8. The apparatus of claim 7, wherein said funnel upper section has a conical shape.

9. The apparatus of claim 1, wherein said vessel has a vertical longitudinal axis and said condenser has a longitudinal axis sloped downwardly from said vessel longitudinal axis for solvent flow from said chamber into and through said condenser.

10. A system for recovering solvent from an oil and grease content analysis of a test sample mixed in a solvent, comprising:
    a separatory funnel for the test sample and solvent mixture;
    a vessel for receiving the solvent and sample mixture from the separatory funnel, the vessel defining a chamber;
    a funnel mounted in said vessel chamber for receiving a filter of the solvent and sample mixture to remove sample from the mixture;
    a fluid conduit extending downwardly from said funnel to convey solvent therefrom;
    a vapor return member with said vessel and mounted extending from said vessel below said funnel, the vapor return member being in fluid communication with said chamber;
    said fluid conduit being mounted in said vapor return member outwardly from said chamber;
    an evaporation flask connectable with said vapor return member and said fluid conduit for receiving solvent from the funnel and providing a supply of solvent;
    a downwardly sloped condenser sealingly engaged with said vessel and being in fluid communication with a lower portion of said chamber for receiving solvent vapors from said chamber; and
    a recovery flask connectable with said sloped condenser for receiving the solvent from the vapors.

11. The system of claim 10, further comprising said funnel having an upper section for holding a filter.

12. The system of claim 11, wherein said vapor return member surrounds the fluid conduit to form an annular space between said fluid conduit and said vapor return member, said annular space providing a pathway for vapor to flow from said evaporation flask into said chamber of said vessel.

13. The system of claim 12 wherein said downwardly sloped member comprises a condenser for vapors evaporated from the solvent.

14. The system of claim 10, further comprising:
    a plurality of vessels for receiving solvent, each vessel having a chamber;
    a funnel mounted in said vessel chamber for receiving a filter of the solvent and sample mixture to remove sample from the mixture;
    a fluid conduit extending downwardly from said funnel to convey solvent therefrom;
    a vapor return member sealingly engaged with each of said vessels, said vapor return member being in fluid communication with said chamber;
    said fluid conduit being mounted in said vapor return member outwardly from said chambers;
    a condenser having an inlet and an outlet, the inlet of each condenser being sealingly engaged with each of said vessels in fluid communication with each chamber for receiving and condensing vapors;
    a manifold connected to the outlet of each condenser for collecting and combining vapors; and
    solvent recovery container in fluid communication with the manifold for receiving and holding solvent.

15. The system of claim 10, further comprising a reflux condenser interposed between said downwardly sloped condenser and said recovery flask, said reflux condenser comprising:
    an elongated tube having tapered joints at each end and a side inlet port;
    a continuous helical coil disposed within the elongated tube, the helical coil having a coil inlet and a coil outlet, wherein the inlet and the outlet protruding through the tube for connection of the coil inlet to a fluid supply, a vapor-tight seal being provided where the coil inlet and the coil outlet protrude through the tube; and
    a side inlet member formed integral with the tube at the side inlet port for providing fluid communication between said downwardly sloped condenser and said elongated tube.

16. The system of claim 15, wherein the side inlet port is positioned in a central portion of the tube.

17. A method for minimizing solvent losses in a closed system when measuring oil and grease content in water, comprising:
    providing in the closed system a separatory funnel having a sealed outlet vessel, the vessel being sealed to a vapor return member, the vapor return member being sealed to an evaporation flask;

extracting the oil and grease with a solvent in said separatory funnel;

receiving the solvent in said evaporation flask from said separatory funnel through said vessel and through said vapor return member;

evaporating the solvent from said evaporation flask;

communicating solvent vapors into said vessel from the evaporation flask through the vapor return member;

condensing the solvent vapors to form a condensate;

preventing condensed solvent from returning to said evaporation flask; and collecting the condensate in a container, wherein the container is in sealed communication with the vessel.

18. The method of claim 17, further comprising the steps of flowing the solvent from the separatory funnel to the evaporation flask; and filtering the solvent within said vessel as the solvent flows.

19. The method of claim 18, further comprising the step of drying the solvent using a chemical drying agent received in a filter held in the funnel.

* * * * *